US007037324B2

(12) United States Patent
Martinek

(10) Patent No.: US 7,037,324 B2
(45) Date of Patent: May 2, 2006

(54) KNOTLESS TISSUE ANCHOR

(75) Inventor: Jonathan Martinek, Hamden, CT (US)

(73) Assignee: United States Surgical Corporation, Norwalk, CT (US)

( * ) Notice: Subject to any disclaimer, the term of this patent is extended or adjusted under 35 U.S.C. 154(b) by 139 days.

(21) Appl. No.: 09/951,069

(22) Filed: Sep. 13, 2001

(65) Prior Publication Data

US 2003/0109900 A1  Jun. 12, 2003

Related U.S. Application Data

(60) Provisional application No. 60/232,714, filed on Sep. 15, 2000.

(51) Int. Cl.
*A61B 17/04* (2006.01)
(52) U.S. Cl. .................. 606/232; 606/148; 606/224; 606/139; 606/60; 606/72
(58) Field of Classification Search ................ 606/72, 606/73, 74, 732, 53, 60, 68, 227–233
See application file for complete search history.

(56) References Cited

U.S. PATENT DOCUMENTS

| | | | | |
|---|---|---|---|---|
| 2,121,193 A | 6/1938 | Hanicke | ....................... | 128/92 |
| 2,381,050 A | 8/1945 | Hardinge | ....................... | 128/92 |
| 2,490,364 A | 12/1949 | Livingston | ................... | 128/92 |
| 2,699,774 A | 1/1955 | Livingston | ................... | 128/92 |
| 3,768,635 A | 10/1973 | Eggert | ......................... | 206/17 |
| 3,910,281 A | 10/1975 | Kletschka et al. | .......... | 128/335 |
| 3,951,261 A | 4/1976 | Mandel et al. | ............... | 206/227 |
| 4,006,747 A | 2/1977 | Kronenthal et al. | ........ | 128/335 |
| 4,135,623 A | 1/1979 | Thyen | ....................... | 206/63.3 |
| 4,244,370 A | 1/1981 | Furlow et al. | .............. | 128/303 |
| 4,275,717 A | 6/1981 | Bolesky | ....................... | 128/92 |
| 4,351,069 A | 9/1982 | Ballintyn et al. | ............ | 3/1.912 |
| 4,424,898 A | 1/1984 | Thyen et al. | ............... | 206/63.3 |
| 4,454,875 A | 6/1984 | Pratt et al. | ..................... | 128/92 |
| 4,519,100 A | 5/1985 | Wills et al. | ..................... | 3/1.9 |
| 4,520,511 A | 6/1985 | Gianezio et al. | ............. | 3/1.913 |
| 4,539,981 A | 9/1985 | Tune | ........................... | 128/92 |

(Continued)

FOREIGN PATENT DOCUMENTS

FR          2622430          5/1989

(Continued)

OTHER PUBLICATIONS

Design News "Ligament Fastener Cuts Recovery Time", vol. 56 p., 8-21 (1989).

(Continued)

*Primary Examiner*—Glenn K. Dawson

(57) ABSTRACT

A radially expandable knotless tissue anchor including an expandable outer member defining a bore and an inner member slidably positioned within the bore. Relative longitudinal movement of the inner member relative to the expandable member causes a portion of the expandable member to expand radially outwardly. The tissue anchor further includes a length of suture material having a first end affixed to a distal end of the inner member and a second end preferably affixed to a suturing needle. A transverse bore is provided adjacent the distal end of the inner member. A method of knotlessly anchoring a section of tissue to a section of bone having a bore drilled therethrough includes passing the suture through the tissue and positioning the expandable member and a section of tissue within the interior of the bore drilled in bone. Expansion of the expandable member secures the suture between the expandable member and the bone to thereby secure the attached tissue to bone.

6 Claims, 8 Drawing Sheets

U.S. PATENT DOCUMENTS

| | | | |
|---|---|---|---|
| 4,550,449 A | 11/1985 | Tune | 623/16 |
| 4,570,623 A | 2/1986 | Ellison et al. | 128/92 |
| 4,586,502 A | 5/1986 | Bedi et al. | 128/334 |
| 4,590,928 A | 5/1986 | Hunt et al. | 128/92 |
| 4,590,930 A | 5/1986 | Kurth et al. | 128/92 |
| 4,591,048 A | 5/1986 | Eldridge, Jr. | 206/63.3 |
| 4,621,640 A | 11/1986 | Mulhollan et al. | 606/144 |
| 4,632,100 A | 12/1986 | Somers et al. | 128/92 |
| 4,655,777 A | 4/1987 | Dunn et al. | 623/16 |
| 4,669,473 A | 6/1987 | Richards et al. | 606/215 |
| 4,699,271 A | 10/1987 | Lincoln et al. | 206/63.3 |
| 4,713,076 A | 12/1987 | Draenert | 623/16 |
| 4,738,255 A | 4/1988 | Goble et al. | 606/86 |
| 4,741,330 A | 5/1988 | Hayhurst | 128/92 |
| 4,760,843 A | 8/1988 | Fischer et al. | 128/92 |
| 4,790,304 A | 12/1988 | Rosenberg | 128/92 |
| 4,828,562 A | 5/1989 | Kenna | 623/13 |
| 4,870,957 A | 10/1989 | Goble et al. | 128/92 |
| 4,871,289 A | 10/1989 | Choiniere | 411/48 |
| 4,895,148 A | 1/1990 | Bays et al. | 606/213 |
| 4,898,156 A | 2/1990 | Gatturna et al. | 606/72 |
| 4,898,505 A | 2/1990 | Froehlich | 411/55 |
| 4,899,743 A | 2/1990 | Nicholson et al. | 606/139 |
| 4,921,383 A | 5/1990 | Fischer | 411/57 |
| 4,927,421 A | 5/1990 | Goble et al. | 606/73 |
| 4,946,468 A | 8/1990 | Li | 606/232 |
| 4,968,315 A | 11/1990 | Gatturna | 606/72 |
| 4,969,892 A | 11/1990 | Burton et al. | 606/218 |
| 4,976,680 A | 12/1990 | Hayman et al. | 606/7 |
| 5,002,550 A | 3/1991 | Li | 606/139 |
| 5,013,316 A | 5/1991 | Goble et al. | 606/72 |
| 5,015,250 A | 5/1991 | Foster | 606/147 |
| 5,037,422 A | 8/1991 | Hayhurst et al. | 606/72 |
| 5,041,129 A | 8/1991 | Hayhurst et al. | 606/232 |
| 5,046,513 A | 9/1991 | Gatturna et al. | 128/898 |
| 5,053,047 A | 10/1991 | Yoon | 606/223 |
| 5,078,730 A | 1/1992 | Li et al. | 606/228 |
| 5,080,543 A | 1/1992 | Murphy | 411/80.5 |
| 5,084,050 A | 1/1992 | Draenert | 606/77 |
| 5,085,661 A | 2/1992 | Moss | 606/139 |
| 5,100,417 A | 3/1992 | Cerier et al. | 606/139 |
| 5,101,421 A | 3/1992 | Nishiki | 378/98.8 |
| 5,102,421 A | 4/1992 | Anspach, Jr. | 606/232 |
| 5,131,533 A | 7/1992 | Alpern | 206/63.3 |
| 5,144,961 A | 9/1992 | Chen et al. | 128/898 |
| 5,156,616 A | 10/1992 | Meadows et al. | 606/232 |
| 5,167,664 A | 12/1992 | Hodorek | 606/73 |
| 5,169,400 A | 12/1992 | Mühling et al. | |
| 5,176,682 A | 1/1993 | Chow | 606/72 |
| 5,207,679 A | 5/1993 | Li | 606/72 |
| 5,209,753 A | 5/1993 | Biedermann et al. | 606/72 |
| 5,217,486 A | 6/1993 | Rice et al. | 606/232 |
| 5,236,445 A | 8/1993 | Hayhurst et al. | 606/232 |
| 5,258,016 A | 11/1993 | DiPoto et al. | 606/232 |
| 5,268,001 A * | 12/1993 | Nicholson et al. | 606/72 |
| 5,354,298 A | 10/1994 | Lee et al. | 606/72 |
| 5,464,427 A * | 11/1995 | Curtis et al. | 606/232 |
| 5,480,403 A * | 1/1996 | Lee et al. | 606/72 |
| 5,486,197 A * | 1/1996 | Le et al. | 606/232 |
| 5,569,301 A | 10/1996 | Granger et al. | |
| 5,618,314 A * | 4/1997 | Harwin et al. | 606/232 |
| 5,645,547 A | 7/1997 | Coleman | 606/73 |
| 5,733,307 A | 3/1998 | Dinsdale | 606/232 |
| 5,782,866 A | 7/1998 | Wenstrom, Jr. | 606/232 |
| 5,868,789 A * | 2/1999 | Huebner | 606/232 |
| 5,928,244 A | 7/1999 | Tovey et al. | |
| 5,964,766 A | 10/1999 | Shaw | 606/73 |
| 6,056,771 A * | 5/2000 | Proto | 606/229 |
| 6,139,565 A | 10/2000 | Stone et al. | 606/232 |
| 6,319,252 B1 * | 11/2001 | McDevitt et al. | 606/60 |
| 2001/0053913 A1 * | 12/2001 | Freedland | 606/73 |
| 2003/0130695 A1 * | 7/2003 | McDevitt et al. | 606/232 |

FOREIGN PATENT DOCUMENTS

| | | |
|---|---|---|
| GB | 2084468 | 9/1981 |
| SU | 584855 | 12/1977 |
| WO | 8603666 | 9/1986 |
| WO | WO 89/09030 | 10/1989 |
| WO | 8910096 | 11/1989 |
| WO | 9204874 | 4/1992 |
| WO | 9308747 | 5/1993 |

OTHER PUBLICATIONS

Mitek, Surgical Products, "Mitek Gil Anchor High Strength Fixation".

Mitek, Surgical Products, "Mitek Quick Anchor Fast, Effective Soft Tissue Reattachment".

Mitek, Surgical Products, "Mitek Anchor System Effective Soft Tissue Reattachment".

Statak™ Soft Tissue Attachment Device.

Acufex Microsurgical, Inc. "Acufex The Leader In Less Invasive Tissue Fixation, Introduces TAG Tissue Anchor Guide System".

Instrument Makar, Inc. "Arthroscopy Equipment and Supplies".

Flynn et al. American Journal of Arthroscopy "Arthroscopically Assisted Rotator Cuff Repair With The Mitek Anchor".

Rob Style Technique Technique For Using Tag™ Tissue Anchor Rob Style.

Arthrex Inc. "The Complete Arthrex Information System".

PCT Search Report.

* cited by examiner

KNOTLESS TISSUE ANCHOR

This application claims priority from Provisional Application Ser. No. 60/232,714 filed on Sep. 15, 2000.

BACKGROUND

1. Technical Field

The present disclosure relates to knotless tissue and suture anchors and, more particularly to radially expandable anchors and methods for use of the expandable anchors.

2. Background of Related Art

During surgery it is often necessary to attach prosthetic implants or soft tissue such as muscle tissue, ligaments, or tendons to hard tissue such as bone. Various types of surgical fasteners are employed for accomplishing this function, including staples, screw and washer systems, suture anchoring devices, and tissue anchors.

The first of these types is illustrated in U.S. Pat. Nos. 4,454,875 and 4,570,623, which show metal staples with spikes on the underside of the crosspiece to secure ligaments.

Fasteners included in the second of these types are available as screw-washer combinations wherein the screw is fabricated from a surgically suitable metal, such as titanium or stainless steel alloy, and is usually of self-tapping design. Suture anchors are adapted to be inserted into predrilled holes in bone and can be made of bioabsorbable material. When securing a ligament or suture within a bore drilled in bone, the self-tapping screws may abrade the ligament or suture as they are threaded in.

Suture anchors are also used to draw tissue adjacent bone. The anchor, having a first end and a suture attached thereto is anchored in bone and a second end of the suture is threaded through tissue and a knot is tied to secure the tissue to the bone.

Expandable tissue fasteners adapted for use in minimally invasive surgical procedures (e.g. arthroscopic procedures) are employed, for example, in the repair of shoulder and knee injuries. In such procedures, the operating instrumentation is usually deployed through a long, narrow cannula inserted through a small incision in the skin. Knots in the suture are typically tied remotely and pushed down to the anchor to secure the tissue and the site.

What is needed is an expandable tissue fastener or anchor for knotlessly securing tissue bone, and for atraumatically securing a graft to bone, especially in minimally invasive surgical procedures.

SUMMARY

What is provided is a knotless tissue anchor including an expandable member defining a bore therethrough and having a radially expandable portion. The expandable member may also have an enlarged head portion. Preferably the radially expanding portion includes at least two distally extending legs defining a pair of slots therebetween. The tissue anchor further includes an inner member slidably disposed within the bore of the expandable member and having a camming surface engageable with the distal ends of the legs to force the distal ends of the legs radially outwardly in response to the distal movement of the expandable member relative to the inner member. The inner member also includes a length of suture having a first end affixed to the distal end of the inner member and a second free end and preferably the second free end is affixed to a surgical needle for passing the suture through tissue. More preferably the second end of the suture is affixed to a double pointed surgical needle or surgical incision member configured to pass the suture through tissue. Importantly, a distal end of the inner member is provided with a transverse bore of sufficient diameter to allow the surgical needle and suture to pass therethrough in order to secure tissue or a length of ligament adjacent the distal end of the inner member.

The proximal end of the inner member may be provided with an enlarged head for engagement and retention within a mounting member associated with an implantation apparatus. Furthermore, the inner member may be provided with a plurality of fins configured to slide within and be guided by the slots defined between the legs of the outer member. Ridges may also be provided on a shaft section of the inner member to prevent a distal movement of the inner member relative to the expandable member after the legs have been expanded. Finally, the inner member may also be provided with a breakaway notch such that upon full expansion of the legs of the expandable member, the notch is severed and a portion of the inner member is broken off to leave the surface of the tissue anchor flush with bone.

There is also provided a mounting member configured to releasably receive the disclosed tissue fastener and to be releasably mounted on an implantation apparatus.

There is also disclosed a method of knotlessly securing a section of tissue to a bone. This is particularly advantageous in surgeries such as shoulder, ligament or muscle repair surgery. The method generally includes providing the disclosed tissue fastener having an expandable outer member defining a bore and the inner member movably mounted within the outer member. Additionally, a length of suture affixed to the distal end of the inner member and having a suturing needle at the opposite end of the suture is also provided. The method further includes the steps of passing the free end of the suture through the tissue to be fastened. Preferably, this is accomplished with a suturing instrument utilized to pass the surgical needle through the tissue. Thereafter, the tissue fastener, having the section of tissue attached thereto, is positioned with a bore formed in bone while the section of tissue remains outside the bore. Additionally, the length of suture extending from the distal end of the inner member is also positioned in the bore formed in the bone and extending parallel to the tissue fastener and outwardly of the bore. The expandable member is expanded by driving the expandable member distally relative to the inner member to thereby expand the expandable member into engagement with the suture against the bone.

The method may also include the step of passing the free end of the suture through a transverse bore in a distal end of the inner member after the suture has been passed through tissue to secure the tissue adjacent the distal end of the inner member. After the suture has been passed through the transverse bore, tension may be applied to the suture to either draw the tissue adjacent the bore drilled in bone.

There is also disclosed a method of securing a ligament within an elongated bore drilled in bone such as that used in knee repair surgery. Method includes providing the tissue fastener described herein and piercing the ligament one or more times with the needle attached to the suture. Thereafter the needle and suture are passed through the hub to a transverse bore in the distal end of an inner member of the tissue fastener and the ligament is snugly secured adjacent the distal end of the inner member. Furthermore, the suture may be wrapped several times about the ligament and distal end of the inner member thereby securely lashing the ligament to the distal end of the inner member. The tissue fastener is either provided with a mounting portion for attachment to an implantation apparatus or may be manually assembled into a mounting member which is then releasably mounted into an implantation member.

Once the assembled tissue fastener and ligament have been mounted on the implantation apparatus, the implantation apparatus may be inserted through an enlarged bore formed through a pair of knee bones. The bores are of sufficient diameter that the attached ligament is not abraded or destroyed as it is advanced through the enlarged bore. Preferably, at the distal most end of the bores, a reduced diameter section is provided for receipt of the tissue fastener and associated ligament. Thereafter the implantation apparatus is actuated to expand the expandable member thus compressing the ligament adjacent the wall of the bore of the bone to secure the ligament between the expandable member and the bone. Thus, the ligament can be implanted with only radially extending forces acting on the ligament thereby providing atraumatic delivery and securement of the ligament within knee bone.

BRIEF DESCRIPTION OF THE DRAWINGS

Various embodiments are described below with reference to the drawings wherein.

DETAILED DESCRIPTION OF PREFERRED EMBODIMENTS

The preferred embodiments of the apparatus and methods disclosed herein are discussed in terms of orthopedic expandable tissue fastener implantation. It is also envisioned, however, that the disclosure is applicable to a wide variety of procedures including, but not limited to ligament repair, joint repair or replacement, non-union fractures, facial reconstruction, etc. In addition, it is believed that the present apparatus finds application in both open and minimally invasive procedures including endoscopic and arthroscopic procedures wherein access to the surgical site is achieved through a cannula or small incision.

In the description which follows, the term "proximal", as is traditional, will refer to the portion of the structure which is closest to the operator, while the term "distal" will refer to the portion which is furthest from the operator.

The device and methods described herein are specifically configured for securing tissue or suture material by applying a radially expandable tissue fastener to a predrilled hole in bone and securing the tissue or suture between the fastener and the bone. The orthopedic tissue fastener is preferably provided as part of a disposable loading unit including a mounting unit.

Figure 1:
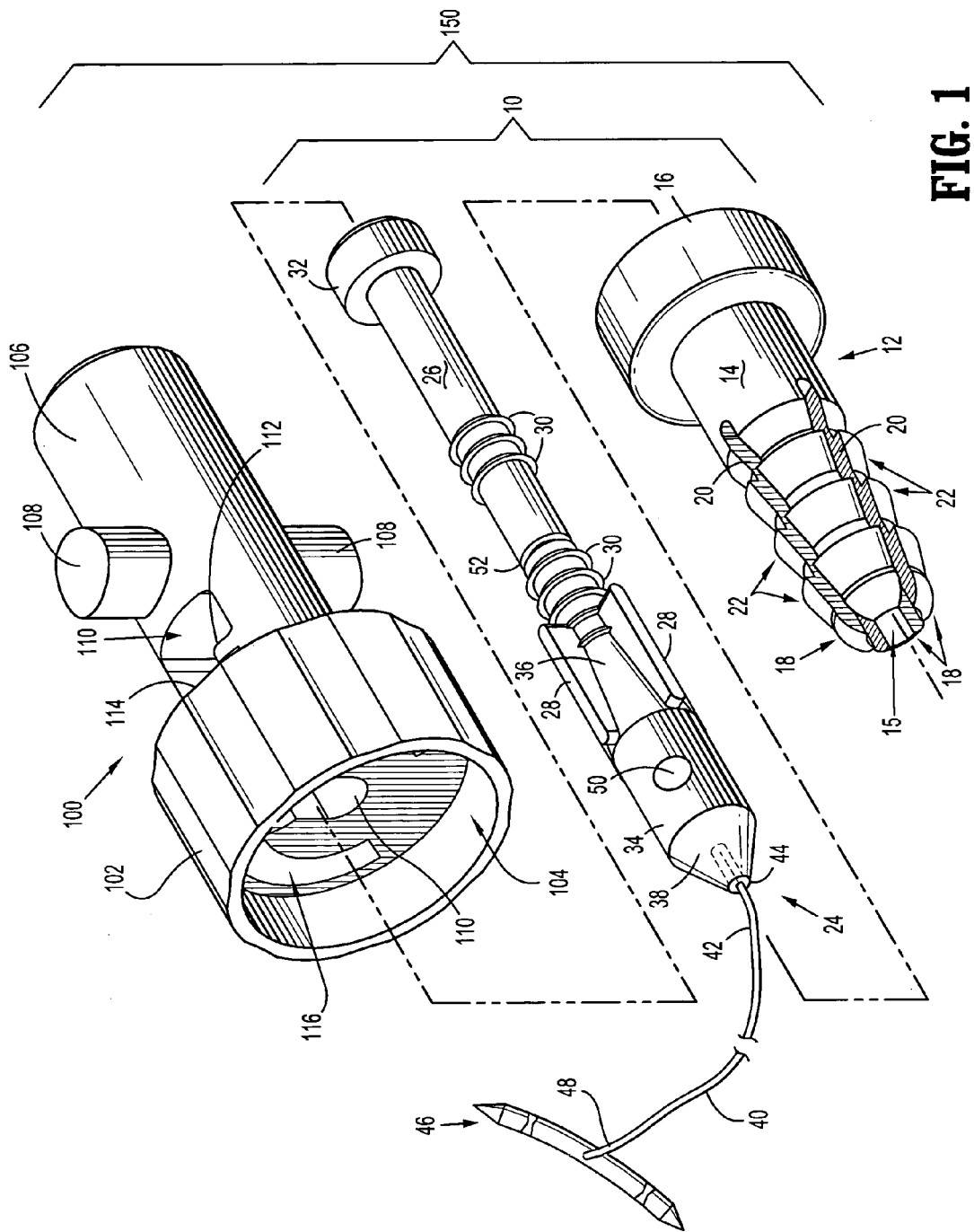
FIG. 1 is a perspective view, with parts separated, of a preferred embodiment of a radially expandable tissue fastener including an associated length of suture and needle and a mounting portion for use with an implantation device.

Referring now to FIG. 1, tissue fastener 10 includes an expandable body 12 and a setting pin. More particularly, body 12 and the setting pin are preferably fabricated from a bioabsorbable material such as polymers of glycolide, lactide, caprolactrone, p-dioxanone, trimethylene carbonate and physical and chemical combinations thereof. Body 12 includes a shaft 14 with an axial aperture 15 extending therethrough. An enlarged head 16 may be provided at a proximal end of shaft 14 to engage an implantation instrument.

Shaft 14 includes at least two, and preferably four, distally extending legs 18 which are defined by lengthwise slots 20. Body 12 is fabricated from a material with sufficient flexibility and resiliency to allow legs 18 to radially expand by splaying outward. When body 12 is placed in a hole and legs 18 are expanded, barbs 22 provided on the outer surface of legs 18 engage the wall of bone tissue surrounding the hole and frictionally secure the body therein. Expanded legs 18 also knotlessly secure a section of suture or graft material positioned between legs 18 and adjacent bone. Legs 18 are expanded in response to engagement with a setting pin 24 as described below.

Setting pin 24 is part of expandable tissue fastener 10 and includes an elongated shaft 26 with at least one, and preferably four, lengthwise extending fins 28 adapted to engage and be guided by slots 20 in body 12. A series of circumferential barbs 30 on the shaft 26 inhibit distal motion of setting pin 14 relative to body 12. Shaft 24 also includes a wider diameter head 32 at its proximal end to facilitate grasping of setting pin 24 by an implantation instrument. At its distal end portion, shaft 26 includes an expanded diameter bulbous portion 34 which includes a proximally facing camming surface 36 and distally facing beveled tip 38. Camming surface 36 is provided to engage and radially expand legs 18 on body 12. A first end 42 of an associated length of suture 40 is affixed to shaft 26 within a bore 44 in tip 38. A needle 46 is affixed to a second end 48 of suture 40. Needle 46 may be a known suturing needle or, preferably, a surgical incision member such as that disclosed in U.S. Pat. No. 5,569,301 to Granger et al., the entire disclosure of which is incorporated by reference herein. A transverse bore 50 for receipt of suture 40 is provided in bulbous portion 38. Shaft 26 also includes a proximal end portion demarcated by a circumferential breakaway notch 52.

A mounting member 100 is provided to mount tissue fastener 10 on an implantation apparatus and together therewith forms a disposable loading unit 150. Mounting member 100 is a tissue fastener mounting portion which is an independent structure for supporting both expandable body 12 of tissue fastener 10 and setting pin 24. The entire disposable loading unit 150 mounts to the distal end of the implantation apparatus, as described below.

Mounting member 100 includes a collar 102 defining a recess 104 into which head 16 of body 12 is received and supported. A shaft 106 defines a lengthwise axis and includes laterally extending bayonet mounting pins 108 for releasably engaging L-shaped slots in the housing tube of an implantation instrument. A mounting slot 110 for retaining setting pin 24 extends lengthwise through collar 102 and includes at least one abutment wall 112 for contacting and retaining head 32 of setting pin 24. An access port 114 enables head 32 to be mounted into mounting slot 110 proximal to abutment wall 112. Mounting member 100 also includes arcuate lengthwise extending access chambers 116 which allow passage therethrough of pusher prongs (discussed below) for contacting and pushing head 16 of body 12.

Figure 2:
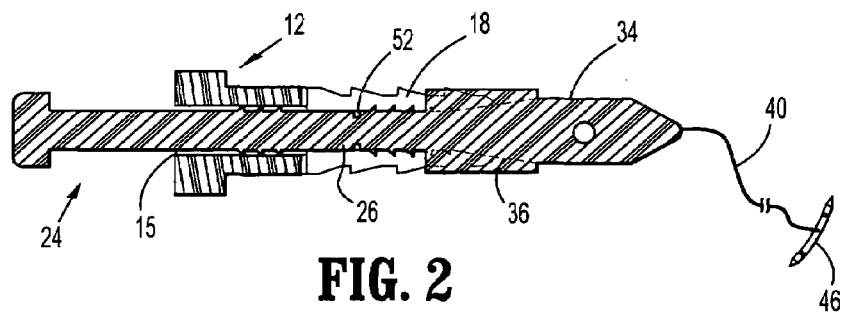
FIG. 2 is a cross-sectional view of the assembled tissue fastener in an unfired state.
Figure 3:
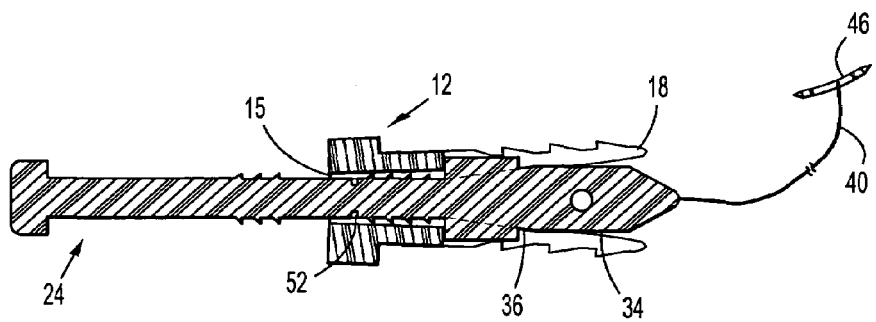
FIG. 3 is a cross-sectional view of the assembled tissue fastener in the radially expanded fired state.

Referring to FIGS. 2 and 3, shaft 26 of setting pin 24 is adapted to be slidably disposed within aperture 15 of body 12. When body 12 is moved distally with respect to setting pin 24, camming surface 36 eventually contacts the distal tips of legs 18. Further distal movement of body 12 causes legs 18 to splay radially apart under the camming action of surface 36 because the diameter of bulbous portion 34 is greater than that of aperture 15. Distal movement of body 12 can be effected by an instrument which distally advances body 12 while holding setting pin 24 stationary, or which grips and pulls head 32 of setting pin 24 while holding body 12 stationary. At a predetermined point, legs 18 are fully expanded and the setting pin 24 cannot move any further through aperture 15. Increased pulling force applied to the proximal end portion of shaft 26 causes shaft 26 to fracture at breakaway notch 52 thereby splitting off the proximal end portion shaft 26 when a predetermined force is applied. Setting pin 24 is configured and dimensioned such that when setting pin shaft 26 undergoes the controlled fracture at full expansion of legs 18, breakaway notch 52 will not be positioned outside aperture 15 of the body 12 but rather within aperture 15.

Figure 4:
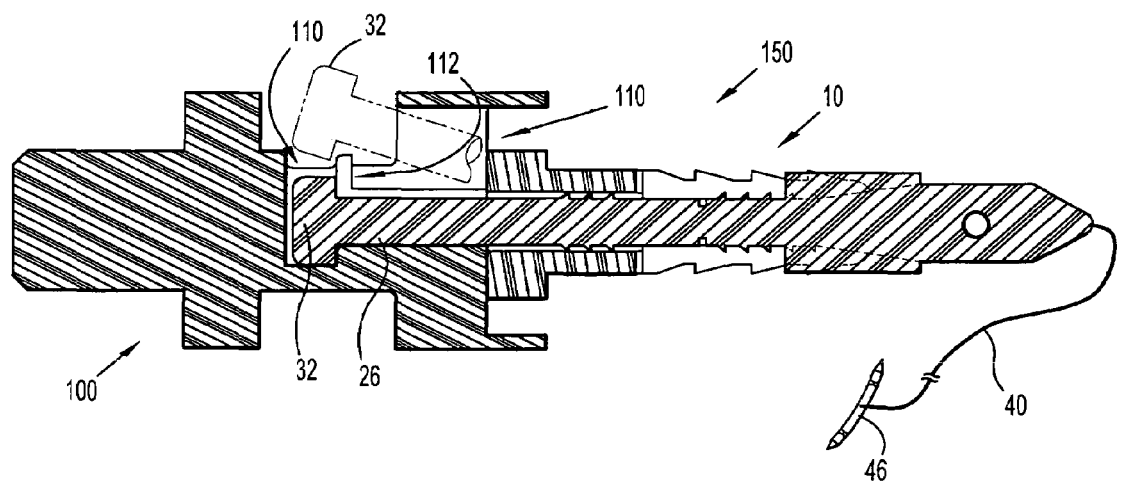
FIG. 4 is a cross-sectional view of the tissue fastener loaded into the mounting portion to form a disposable loading unit.

Referring now to FIG. 4, disposable loading unit 150 is provided to the surgeon in sterilized form and may arrive fully assembled with tissue fastener 10 positioned in mounting member 100 or the components may be separated requiring assembly.

In order to assemble tissue fastener 10 within mounting member 100, elongated shaft 26 of setting pin 24 is inserted into keyhole shaped mounting slot 110 in mounting member 100. Elongated shaft 26 is advanced within slot 10 until head 32 is flexed to a position down into slot 110 and abuts abutment wall 112. Thus, head 16 of expandable body 12 is positioned within recess 104 in collar 102. In this manner the disposable loading unit is assembled and is ready for insertion into an implantation instrument. Attached suture 40 and needle 46 may be provided loose or may be provided in a separate loading unit to facilitate loading needle 46 into a surgical suturing instrument.

Figure 5:
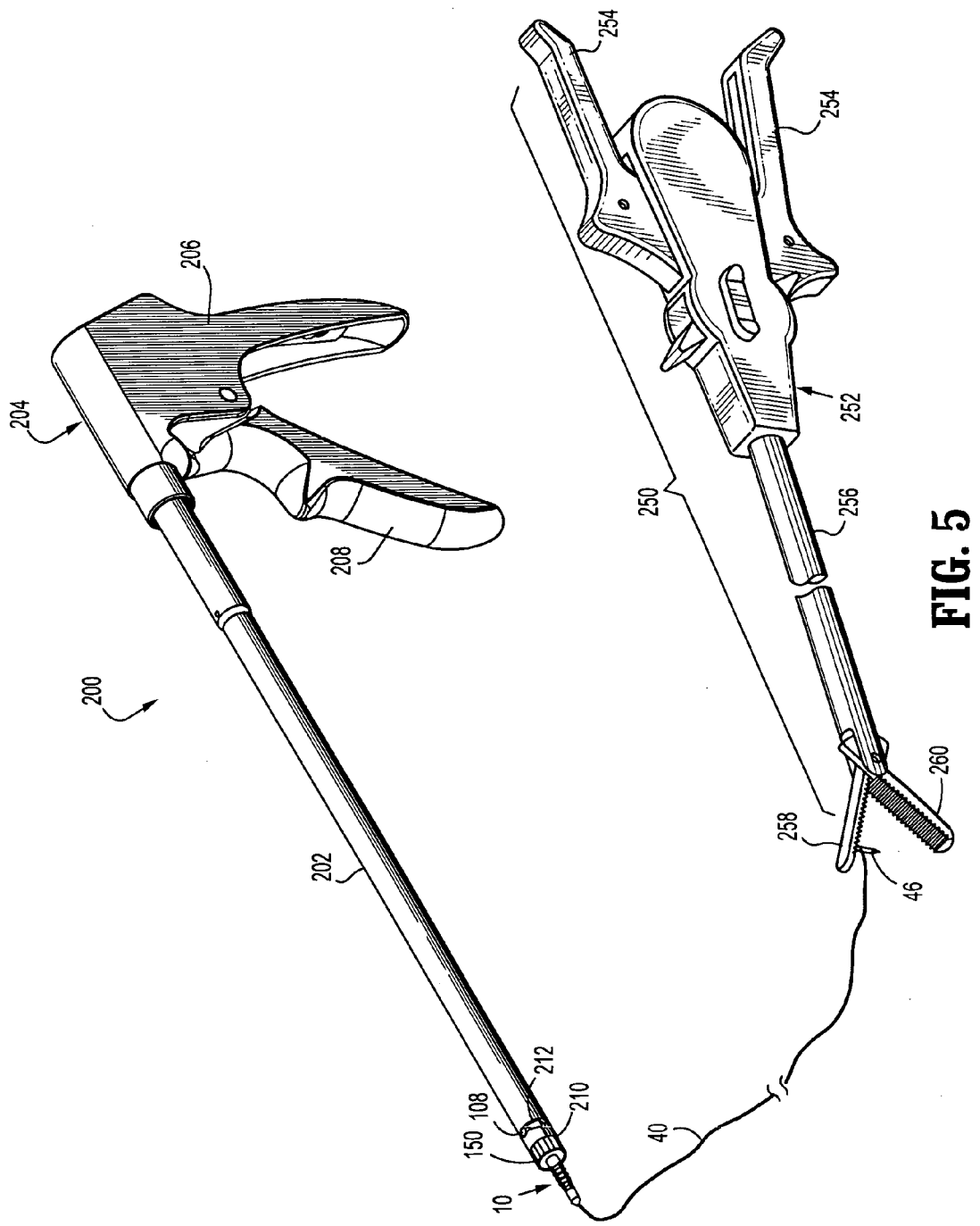
FIG. 5 is a perspective view of the disposable loading unit mounted on a tissue fastener implantation apparatus and the associated needle mounted on a jaw of a suturing apparatus.

Referring now to FIG. 5, there is disclosed a suitable tissue fastener implantation apparatus 200, the components and operation of which are more fully described in U.S. Pat. No. 5,928,244 to Tovey et al., the entire disclosure of which is incorporated by reference herein. In general, implantation apparatus 200 includes an elongated portion 202 extending distally from a handle portion 204. Handle portion 204 generally includes a stationary handle portion 206 and a trigger 208. Operation of trigger 208 acts as operating structure to expand tissue fastener 10.

A distal end of elongated portion 202 is provided with an L-shaped slot 210 configured to receive bayonet mounting pins 108 of mounting member 100. In order to assemble on disposable loading unit 150 into implantation apparatus 200, mounting member 100 is positioned and advanced into the distal end of elongated member 202 such that bayonet mounting pins 108 enter elongated slot 210. Mounting member 100 is then rotated such that bayonet pins 108 are rotated into the transverse portion 212 of slot 210. Thus, the disposable loading unit 150 including mounting member 100 and tissue fastener 10 are securely attached to the distal end of implantation apparatus 200. As noted above, operation of trigger will drive expandable body 12 distally relative to setting pin 24 to thereby expand legs 18 radially outward.

As noted hereinabove, tissue fastener 10 includes a length of suture 40 and a needle 46. Needle 46 may be of any suitable tissue suturing variety. However, the preferred needle 46 is a surgical incision member 46 of the type noted in U.S. Pat. No. 5,569,301 the contents of which were incorporated by reference hereinabove. When utilizing surgical incision member 46, the use of a particular suturing apparatus disclosed in U.S. Pat. No. 5,569,301 is advantageous. Suturing apparatus 250 generally includes a handle portion 252 having a pair of pivoting handles 254 affixed thereto. An elongated member 256 extends distally from handle portion 252 and terminates in a pair of removable jaws 258 and 260. Actuation of handles 254 opens and closes jaws 258 and 260. As discussed in U.S. Pat. No. 5,569,301, operation of a toggle lever 262 functions to releasably and alternatively secure surgical incision member 46 within jaws 258 and 260. Thus, by closing handles 254, jaws 258 and 260 close and cause surgical incision 46 to penetrate tissue positioned therebetween, upon operation of toggle lever 262, surgical incision member 46 can be released from a first jaw and secured in a second jaw to thereby pass the needle through tissue upon opening of jaws 258, 260.

Figure 6:
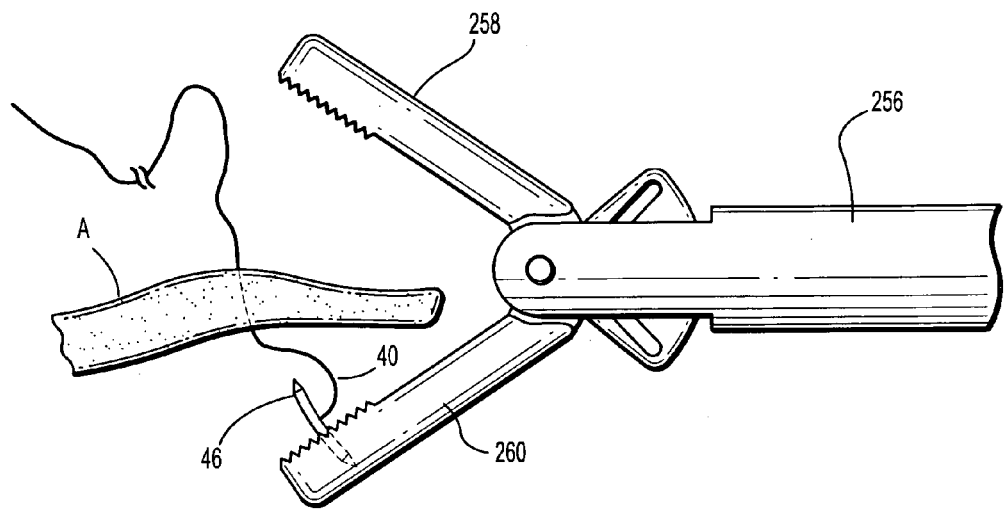
FIG. 6 is a side view of the jaws of the suturing apparatus passing the needle through a section of tissue to be fastened to bone.

Referring now to FIG. 6, the use of tissue fastener 10 to secure a piece of tissue such as muscle tissue relative to bone will now be described. While this discussion has broad applicability to any situation where muscle tissue, ligaments or other soft tissue are to be secured to bone, the following discussion is in terms of securing tissue adjacent a bore drilled in bone as in typical shoulder surgeries. As shown in FIG. 6, the suturing apparatus has been operated to pass surgical incision member 46 and a portion of associated length of suture 40 through a tissue section A. As more fully discussed in U.S. Pat. No. 5,569,301, this is accomplished by positioning the surgical incision member in jaw 258, operating suturing apparatus 250 to close jaws 258 and 260 together so as to pierce tissue section A with surgical incision member 46 and actuating the surgical suturing instrument so as to release surgical incision member 46 from upper jaw 258 and securely grasping it in lower jaw 260, thus on opening of jaws 258 and 260 surgical incision member 46 and portion of suture 40 is pulled through tissue section A.

Figure 7:
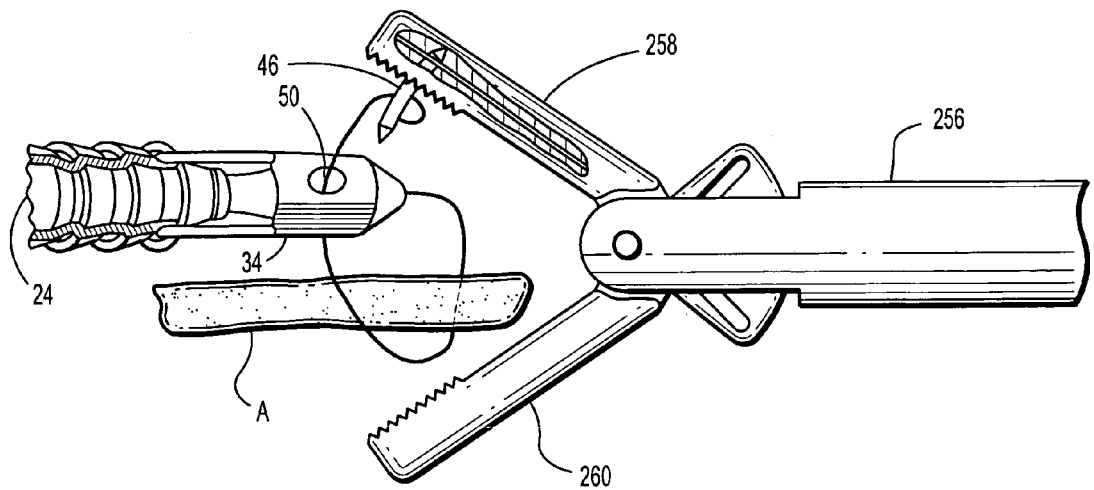
FIG. 7 is a side view of the suturing instrument having passed the needle through a bore in the tissue fastener.

Referring now to FIG. 7, in order to secure tissue section A to distal end of setting pin 24, suturing apparatus 250 is again operated so as to pass surgical incision member 46 through bore transverse 50 in bulbous portion 34 of setting pin 24. By manipulating surgical suturing apparatus 250, tension may be applied to suture 40 so as to draw tissue section A tightly against the distal end of setting pin 24.

Figures 8, 9, 10:
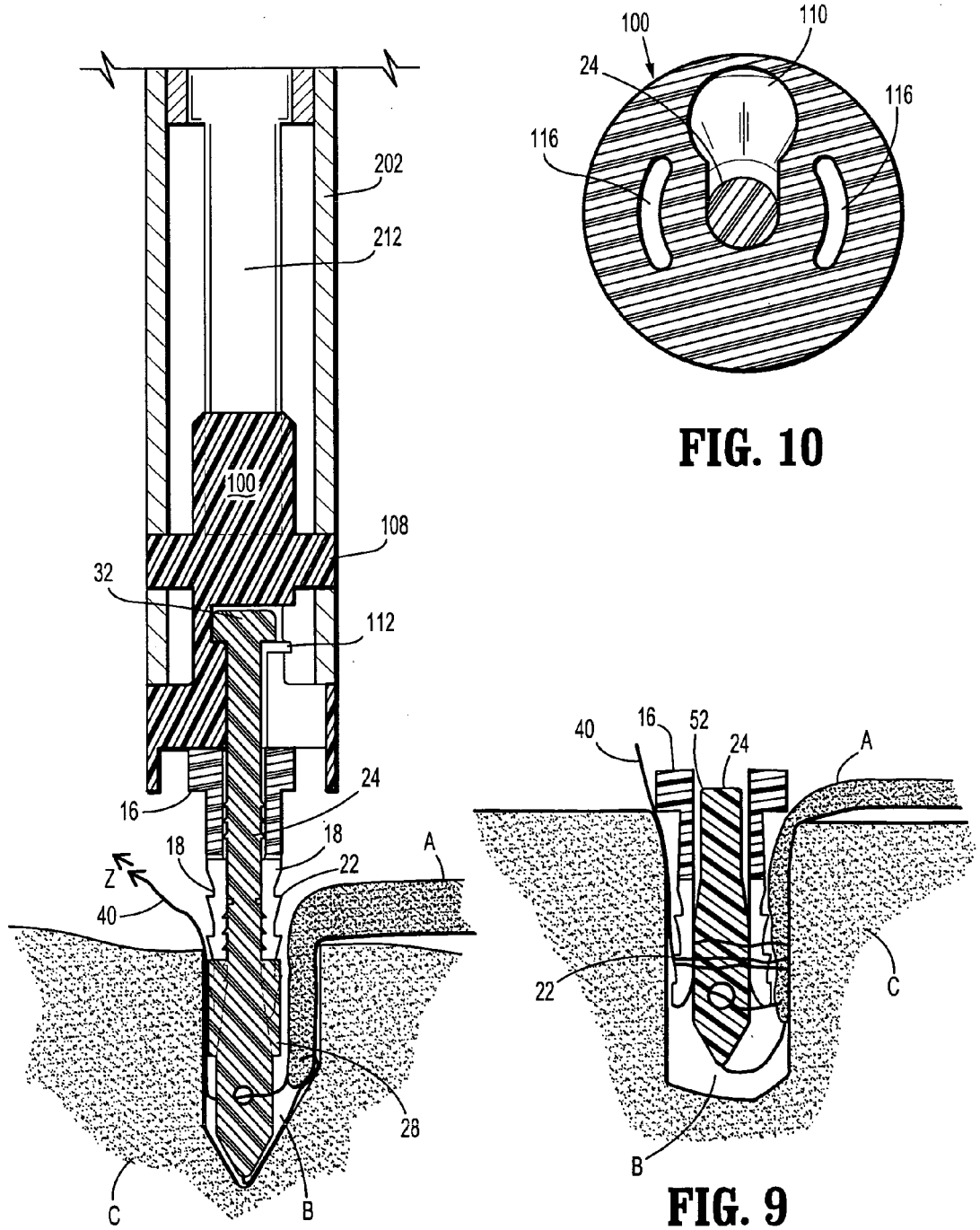
FIG. 8 is a cross-sectional view of the tissue fastener in an unfired state, positioned in a bore drilled in bone.
FIG. 9 is a cross-sectional view of the tissue fastener in the bore formed in the bone, in the fired state, to anchor both ends of the suture therein.
FIG. 10 is a cross-sectional view taken along line 10—10 of FIG. 9.

Referring now to FIG. 8, in order to secure and draw a tissue section adjacent a particular section of bone, a bore B is drilled in the desired section of shoulder bone C. Once a bore B has been drilled in bone C, implantation apparatus 200 can be manipulated so as to position the unfired tissue fastener 10 having a length of tissue A secured adjacent to it within bore B.

Referring to FIGS. 8–10, actuation of implantation apparatus 200 drives a pair of pusher prongs 212 through access chamber 116 in mounting member 100 to engage head 16 of expandable member 12 and thus drive expandable member 12 distally relative to setting 24. Mounting member 100 may have access chamber 116 tapered toward the center of member 100 to allow use with existing instrumentation and engage the relatively small diameter head 16 of expandable member 12. As noted hereinabove, when tissue fastener 10 is loaded in mounting member 100, head 32 of setting pin 24 is restrained from movement. Thus, as the prongs drive expandable member 12 distally, the distal ends of legs 18 are engaged by camming surface 36 on setting pin 24 and driven radially outwardly. As noted above, fins 28 are engaged and are guided by slots 20 formed in expandable member 12. As legs 18 are driven radially outward, barbs 22 engage and secure a portion of suture 40 against the bone C within bore B. Alternatively tissue section A may be drawn into bore B prior to expanding expandable member 12. As discussed above, when sufficient force has been applied to expandable member 12 by pusher prongs, expandable member 12 can advance no further relative to setting pin 24 and the additional force severs or breaks setting pin 24 at breakaway notch 52.

As shown in FIG. 9, after actuation, setting pin 24 is disposed inwardly of head 16 of expandable member 12. In this manner, the section of tissue A is secured adjacent the opening of the bore in bone C. The suture 40 will be sufficiently tensioned so that the tissue section A remains outside the bore. Thus tension can be provided to suture 40 so as to snug an extreme end of the tissue section adjacent tissue fastener 10 without drawing it down into the bore. Actuation of the expandable member 12 secures and locks the suture in place within bore B thereby facilitating securement of the tissue section without the need for any external knots. Thus, this is a convenient, secure and easy knotless suture securing procedure.

Figure 11:
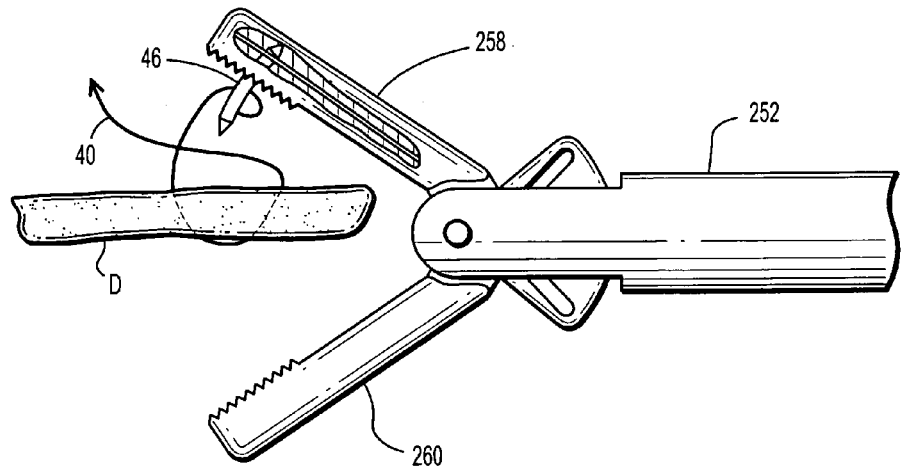
FIG. 11 is a side view of a piece of ligament or graft material having been penetrated by the needle and suture associated with the tissue fastener.

Referring now to FIG. 11, the use of tissue fastener 10 in knee ligament repair surgery where it is desirable to secure a distal end of a ligament within an elongated bore drilled in a knee bone will now be described. As noted above, often this is accomplished by threading a screw adjacent the ligament thereby abrading the ligament or by wedging the ligament together with some sort of wedge into the bore in which event the ligament must travel a longitudinal distance while being abraded by bone on one side and the wedge on the other. The disclosed method has the distinct advantage of being able to position a ligament section within a bore in a knee bone without any trauma to the ligament.

As shown in FIG. 11, initially surgical suturing apparatus 250 is actuated and so as to pass surgical incision member 46 and thus suture 40 through ligament section D. Preferably, surgical incision member 46 is passed back and forth through ligament section D several times so as to gain a secure hold of ligament D with suture 40.

Figure 12:
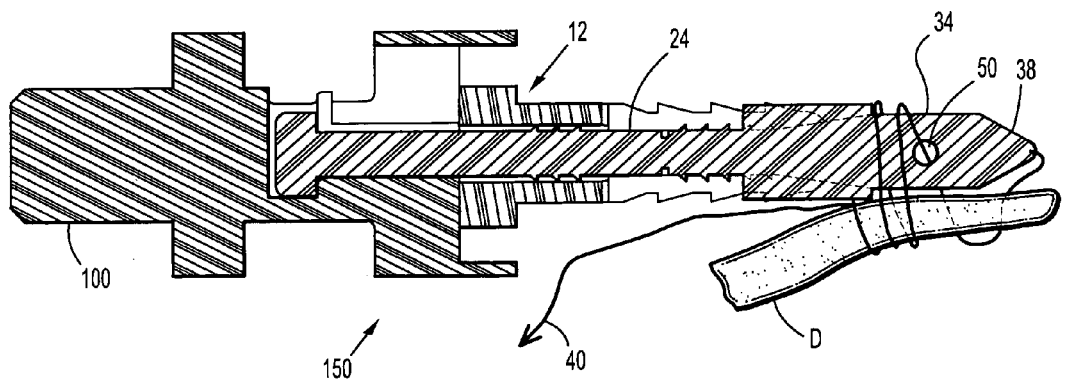
FIG. 12 is a partial cross-sectional view of the graft material secured to an end of the tissue fastener.

Referring now to FIG. 12, ligament section D is advanced along suture 40 towards beveled tip 38 until the pierced section of ligament D is adjacent beveled tip 38. Thereafter, in order to firmly secure ligament section D to setting pin 24 the suturing apparatus is actuated to pass surgical incision 46 through transverse bore 50 in setting pin 24. The suture may then be wrapped around bulbous portion 34 and ligament D numerous times to thereby lash ligament D to the distal end of setting pin 24.

Subsequently, disposable loading unit 150 containing the attached ligament D is mounted to the implant apparatus as described above.

Figure 13:
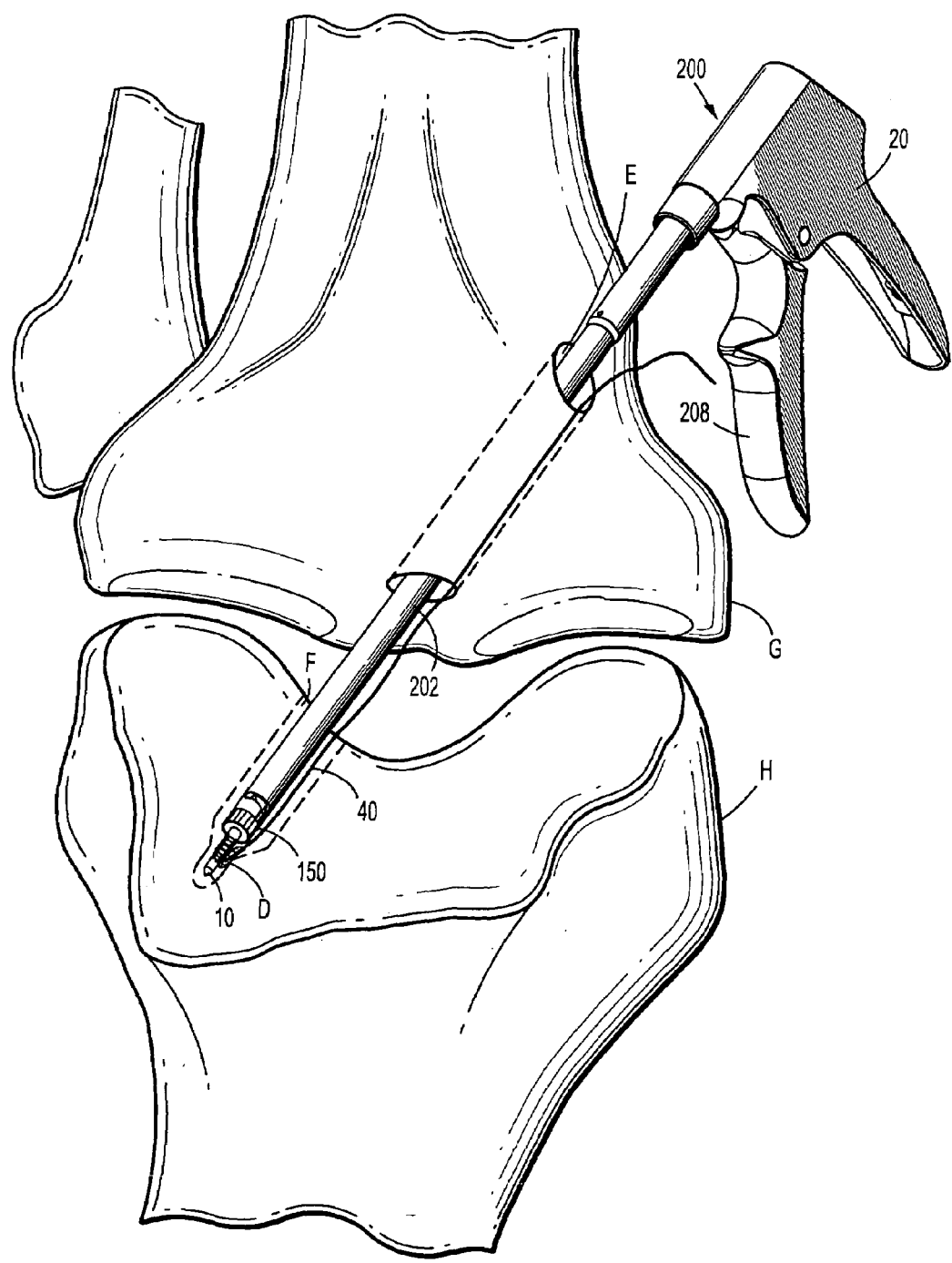
FIG. 13 is a perspective view of the assembled tissue fastener and graft material mounted on the implantation apparatus and positioned in a bore drilled through bone.

Referring now to FIG. 13, once disposable loading unit 100 and apparatus 200 have been assembled, implantation apparatus 200 is positioned such that elongated portion 202 and tissue fastener 10 are advanced through bores E and F drilled through knee joints G and H. Specifically shown in FIG. 13, bores E and F through the knee bone sections are of sufficient diameter such that elongated portion 204 may be passed therethrough. However, because of the reduced diameter of tissue fastener 10 and ligament D, the ligament is not traumatized as it is advanced through bones E and F. A smaller diameter bore 1 is drilled at the end of bore F to accommodate them. The point at which the implant is to be expanded is in the reduced diameter bore I.

Figure 14:
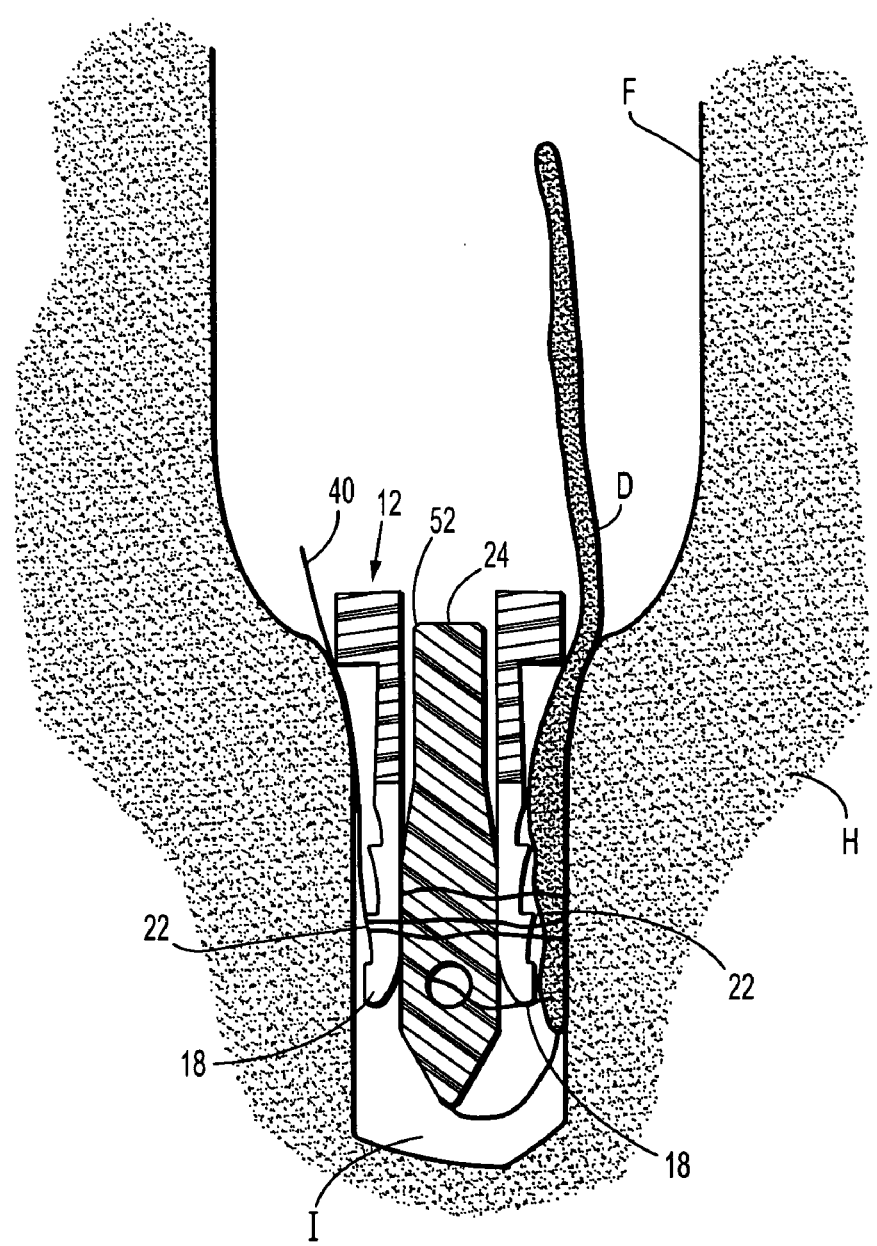
FIG. 14 is a partial cross-sectional view of the expanded tissue fastener securing a first end of the graft material within the bore in the bone.

Referring to FIGS. 13 and 14, actuation of implantation apparatus 200 will operate to push expandable member 12 distally relative to setting pin 24 thereby forcing legs 18 radially outwardly to engage and secure ligament section D adjacent to bone G. Thus, ligament D is firmly secured within bore F in sutureless fashion without trauma to ligament D and no additional knots need be tied.

It will be understood that various modifications may be made to the embodiments disclosed herein. For example, barbs 22 are an expandable member. 12 may be reconfigured as abraded surfaces or other means to frictionally engage suture 12 when cammed against suture 12 in a bore in bone. Additionally, barbs 22 may assume a rounded configuration to be less traumatic to any associated ligament or tissue section engaged by legs 18 as they expand. The above description should not be construed as limiting, but merely as exemplifications of preferred embodiments and methods. Those skilled in the art will envision other modifications and uses within the scope and spirit of the claims appended hereto.

What is claimed is:

1. A knotless tissue anchor comprising:
an expandable member defining a bore therethrough and including a shaft and a radially expandable portion extending from the shaft;
an inner member slidably disposed within the bore of the expandable member, the inner member extending completely through the expandable member such that a distal end of the inner member extends beyond a distal end of the expandable member and a proximal end of the inner member extends beyond a proximal end of the expandable member such that the expandable portion expands radially outwardly in response to longitudinal motion of expandable member relative to the inner member; and
a length of suture having a first end and a second end, the first end of the suture being affixed to the distal end of the inner member.

2. The knotless tissue anchor as recited in claim 1, wherein the expandable portion includes at least two flexible legs.

3. The knotless tissue anchor as recited in claim 2, wherein the inner member has a camming surface configured to engage the at least two flexible legs to force ends of said legs radially outward in response to relative longitudinal motion between the expandable member and the inner member.

4. The knotless tissue anchor as recited in claim 3, wherein the camming surface engages the at least two legs in response to distal movement of the expandable member relative to the inner member.

5. The knotless tissue anchor as recited in claim 1, wherein the length of suture extends from the distal end of the inner member and externally of the expandable member.

6. The knotless tissue anchor as recited in claim 1, wherein the expandable member and the inner member are formed from a bioabsorbable material.

* * * * *